United States Patent [19]

Eckhart et al.

[11] 4,226,229
[45] Oct. 7, 1980

[54] ANATOMY TESTING DEVICE

[75] Inventors: Thomas D. Eckhart, R.R. 2, Nevada, Iowa 50201; Richard L. Nelson, Oelwein; Jack M. Hoglan, Independence, both of Iowa

[73] Assignee: Thomas D. Eckhart, Nevada, Iowa

[21] Appl. No.: 892,264

[22] Filed: Mar. 31, 1978

[51] Int. Cl.² ............................................. A61B 10/00
[52] U.S. Cl. ....................................... 128/66; 73/612
[58] Field of Search .......... 128/2 V, 2.05 Z, 660–663; 73/609–617

[56] References Cited

U.S. PATENT DOCUMENTS

| | | | |
|---|---|---|---|
| 3,763,463 | 10/1973 | Muir | 128/2 V X |
| 3,813,926 | 6/1974 | Stobbemon | 73/609 X |
| 3,821,891 | 7/1974 | Collins et al. | 73/612 X |
| 3,914,986 | 10/1975 | Ota et al. | 73/611 X |
| 3,955,405 | 5/1976 | Coutore | 73/609 X |
| 3,964,297 | 6/1976 | Jorgensen et al. | 73/612 X |
| 4,112,927 | 9/1978 | Carlson | 73/614 X |
| 4,138,999 | 2/1979 | Eckhardt et al. | 128/660 |

Primary Examiner—Robert W. Michell
Assistant Examiner—Francis J. Jaworski

Attorney, Agent, or Firm—Zarley, McKee, Thomte, Voorhees & Sease

[57] ABSTRACT

An anatomy testing device for determining pregnancy in gilts and sows is disclosed comprising a housing containing an electronic circuit to generate and analyze ultrasonic waves. Located on the exterior of the housing are a transducer probe for emitting ultrasonic waves when in contact with the animal's body, a first light to indicate that proper airless contact has been made between the animal's body and the probe, a second light to indicate pregnancy of the animal because of the increase in fluid content of the uterus, an audible alarm to also indicate pregnancy, a charger plug for recharging the batteries, and a test button to activate the electronic circuit. The circuit comprises an ultrasonic transceiver monolithic integrated circuit, an inverter means, a binary counter means, two AND gate means and R.S. flipflop means to generate, transmit, receive the echo of, analyze, and interpret ultrasonic waves to determine animal pregnancy. The portable anatomy testing device contains a rechargeable battery power supply within the housing to power the electronic circuit, indicator lights and audio indicator.

8 Claims, 3 Drawing Figures

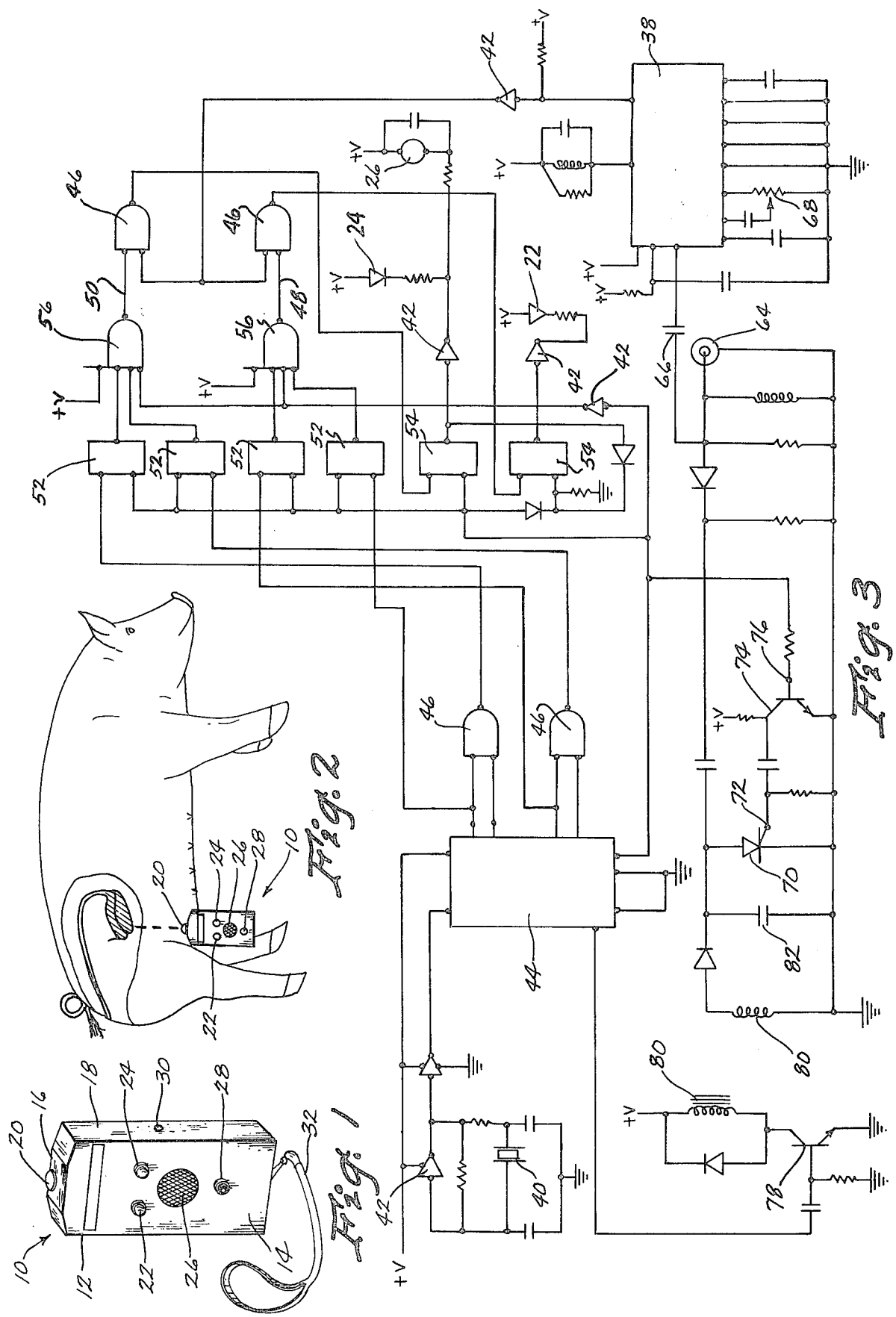

ANATOMY TESTING DEVICE

BACKGROUND OF THE INVENTION

The invention relates to anatomy testing devices and more particularly to a portable self-contained testing device to determine a pregnancy condition in an animal through the use of ultrasonic waves.

Previous testing devices utilizing ultrasonic waves were bulky and cumbersome in size, and remotely located from the animal during testing so as to require a connecting cord between the unit and the transducer located on the animal. The fragility of the transducer connecting cords was a major cause of unit malfunction. Previous devices utilized cathode ray tubes as a display device thereby requiring large power supplies and complex support circuitry. Cathode ray tubes are inconvenient to use in sunlight and often require sun shields for viewing. Previous devices do not provide the quick, easy, one man testing and indication needed for operation during the brief time the animal can be held in the proper position

SUMMARY OF THE INVENTION

A portable self-contained anatomy testing device is disclosed wherein an electronic circuit is contained with a housing having exterior dimensions conducive to hand held operation. The exterior of the housing comprises a transducer probe for airless contact with the animal's body, a first indicator light to indicate the proper contact of the probe with the animal body, a second indicator light to indicate a positive pregnancy test, an audio alarm to also indicate positive pregnancy test, a plug for connection to a battery charger, and a test button to activate the electronic circuit. The electronic circuit comprises an ultrasonic transceiver monolithic integrated circuit, inverter means, binary counter means, And gate circuit means, an R.S. flipflop circuit means, and a cordless transducer to generate, transmit, receive, process and interpret the ultrasonic waves. The electronic circuit compares the transmitted pulses to the received echo in both amplitude and frequency to determine the proper probe contact and to determine relative animal body density for an indication of pregnancy.

It is a principal object of the invention to provide an anatomy testing device that determines the condition of pregnancy in an animal by the processing of ultrasonic waves.

A further object of the invention is to provide an anatomy testing device that is portable and capable of easy, quick hand held operation.

A still further object of the invention is to provide an anatomy testing device that utilizes an electronic circuit having an ultrasonic transceiver monolithic integrated circuit, an inverter means, a binary counter means, an R.S. flipflop means, And gate means to generate, transmit, receive, process and interpret ultrasonic wave impulses.

A still further object of the invention is to provide a hand held anatomy testing device, utilizing a cordless transducer probe.

A still further object of the invention is to provide a rechargeable battery operated portable anatomy testing device for determining the pregnancy of sows and gilts.

A still further object of the invention is to provide an anatomy testing device that is capable of one man hand held operation with visual and audio indication of a condition of pregnancy.

A still further object of the invention is to provide an anatomy testing device that is economical to manufacture, refined in appearance, simple in operation, and durable in use.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings in which:

FIG. 1 is a perspective view of the device of this invention.

FIG. 2 is a view of a sow being tested for pregnancy.

FIG. 3 is an electrical schematic of the circuitry of the device of this invention.

DESCRIPTION OF THE PREFERRED EMBODIMENT

The numeral 10 refers to the anatomy testing device of this invention as shown in FIG. 1. The housing 12 of device 10 is comprised of a face 14, top surface 16, and side surfaces 18. Housing 12 is generally of rectangular shaped aluminum construction with top surface 16 exhibiting a slight convex shape to facilitate the positioning of transducer probe 20 against the animal body. Transducer probe 20 is located on top surface 16 as shown in FIG. 1.

Contact indicator light 22, pregnancy indicator light 24, audio pregnancy indicator 26, and test button 28 are located on front face 14 of device 10 as shown in FIG. 1. Battery charger plug 30 is located on side surface 18 and wrist strap 32 is pivotally attached to bottom surface 34 of testing device 10.

Anatomy testing device 10 determines pregnancy by detecting the increase in fluid content of the uterus of a sow. The amount of amniotic fluid in the uterus increases rapidly from 30 to 80 days after conception of a sow. As will be more fully described hereinafter, a narrow beam of high frequency sound is transmitted into the sow. The echos which bounce back from inside the sow are analyzed and compared to detect the presence of fluid and fetus in the uterus.

The generation, transmission, reception and analysis of the ultrasonic impulses is accomplished by the electronic circuit schematically shown in FIG. 3. The heart of electronic circuit 36 is the ultrasonic transceiver monolithic integrated circuit chip 38. Electronic circuit 36 is particularly designed for the transceiver chip 38 produced by National Semiconductor Corporation type LM 1812, although similar chips may be utilized with minor circuit variations.

A one megahertz crystal 40 is used to provide a stable oscillator with inverter 42 that is used to drive binary counter 44. The particular lines out of the binary counter 44 are gated by AND gate 46 to provide pulses at 64 microseconds, 128 microseconds, 160 microseconds and 320 microseconds. These particular time pulses are used to stop and start the contact window designated by the numeral 48 and the pregnancy window designated by the numeral 50 respectively. These timing pulses are fed into RS flipflops 52 and 54. The output of flipflops 52 and 54 are then fed into AND gate 56. Flipflops 52 and 54 are either set or reset depending upon whether it is the stop or start of the contact window 48 or the pregnancy window 50. The output of AND gate 56 then is used to run AND gate 46. These particular gates have the pregnancy window and the contact window anded with the signal from the transceiver chip 38. If it is a particular window, say the contact window 48, and if there is a signal present, then the output of the gate will go high, that particular signal then is run into RS flipflop 54 whose output is inverted by inverter 42. The output of inverter 42 is then used to directly drive the particular light emitting diode (LED), which in this case is diode 22 for contact, and in the case of pregnancy, diode 24, and the audio Sonalert 26. The Sonalert utilized is a type SN P428 manufactured by Mallory.

Transducer 64 is coupled into transceiver 38 through a 0.01 microfarad capacitor 66. The gain is controlled by a 10K trimpot resistor 68 and the output of transceiver 38 is fed back into the particular AND gate arrangement to provide either a contact or a pregnancy signal. Transducer 64 is triggered through SCR 70 whose gate 72 is controlled by transistor 74. The base 76 of transistor 74 is driven directly by $44_1$ of binary counter 44. The high voltage that is gated through transducer 64 and SCR 70 is provided by transistor 78 which switches current through audio transformer 80 having a 500 ohm primary and an 8 ohm secondary. This switching arrangement allows the high voltage on the 0.01 microfarad capacitor 82 to approach 80 volts. At the appropriate time, this 100 volts on capacitor 82 is discharged through SCR 70 and the 2.25 megahertz transducer crystal.

The particular semiconductors utilized in circuit 36 are: Motorola MC14049BCP for inverter 42, Motorola MC 14040BCP for binary counter 44, Motorola MC 14082BCP for AND gate 56, Motorola MC 14043BCP for R.S. Flipflops 52 and 54, and Motorola MC 14081BCP for AND gate 46, although other devices displaying similar characteristics and performing similar functions may be with or without circuit variations.

To test the animal for pregnancy, contact oil is placed on probe 20 to insure airless contact between the sow's body and the probe. The oil may be clean motor oil or vegetable oil. The probe 20 is placed against the sow's body at a point halfway between the teat line and the side just below the flanks approximately two inches in front of the ham as indicated in FIG. 2. Testing button 28 is then depressed, sending an ultrasonic beam into the body of the sow. If proper contact is made, the returning echo of predetermined amplitude due to the physical tissue characteristics of the sow will be received during the 64 to 128 microseconds contact window. The reception of this echo pulse of predetermined amplitude relative to the transmitted pulse is then indicated by the illumination of LED 22 as noted as contact indicator light 22 on the front face 44 of testing device 10. This informs the user that proper contact of the probe 20 to the sow has been made.

If the sow is pregnant, echos from the presence of amniotic fluid and fetus in the uterus will be received during the 160 to 320 microsecond pregnancy window. The reception of a predetermined number of echo pulses of the predetermined relative amplitude during the 160 microsecond to 320 microsecond pregnancy window indicates a positive pregnancy test and illuminates LED 24 noted as pregnancy indicator light 24 on the front face 14 of device 10 and activates the audio Sonalert 26 to provide the user with both audio and visual indication of pregnancy. By rotating the probe 20 back and forth, the ultrasonic beam scans across the mid-section of the body cavity of the animal to obtain echos from the uterus.

Thus, it can be seen that testing device 10 provides easy, quick, simple hand held pregnancy testing of an animal by a single person, thereby accomplishing at least all of its stated objectives.

What is claimed is:

1. A pregnancy testing device comprising:
    a housing having an outer surface, said housing being of a size capable of being held in one hand;
    a transducer probe located on said outer surface of said housing,
    a first indicator light on said housing for indicating proper contact of said probe with an animal's body;
    a second indicator light on said housing to indicate a positive pregnancy in said animal;
    an audio alarm on said housing for indicating a positive pregnancy in said animal;
    a circuit means within said housing for actuating said probe to transmit ultrasonic pulses into said animal and to receive echo pulses sensed by said probe;
    a first analyzer portion of said circuit means for analyzing echoes received during a first time interval from said pulses transmitted into said animal, said first analyzer portion of said circuit being connected to said first indicator light and being adapted to turn on said first indicator light during said first time interval in response to receipt of echoes of predetermined characteristics caused by the tissue of said animal;
    a second analyzer portion of said circuit means for receiving and analyzing echo signals during a second interval of time from said pulses transmitted into said animal, said second analyzer portion being connected to said second indicator light and said audio alarm and being adapted to turn on said second indicator light and said audio signal during said second time interval in response to echoes of predetermined characteristics caused by amnion fluid in the uterus of said animal; and
    power means within said housing for powering said circuit means.

2. The device of claim 1 wherein said circuit means comprises a monolithic integrated circuit ultrasonic transceiver.

3. The device of claim 1 wherein said second predetermined time interval is from 64 microseconds to 128 microseconds after transmission of said pulses into said animal.

4. The device of claim 3 wherein said first visual indicator means is a light emitting diode.

5. The device of claim 4 wherein said first predetermined time interval is from 160 microseconds to 320 microseconds after transmission of said pulses into said animal.

6. The device of claim 5 wherein said second visual indicator means is a light emitting diode.

7. The device of claim 1 wherein said means to power said circuit comprises a battery.

8. A method of testing an animal for pregnancy comprising:
    providing a portable testing device substantially contained within
        a housing of a size capable of being held in one hand and including a transducer probe on the outside surface of the housing,
    holding said testing device in one's hand, moving the testing device housing into engagement with said animal so as to establish contact between said transducer probe and the animal's body;

transmitting ultrasonic pulses into said animal by means of said transducer probe;

receiving echoes of said transmitted pulses during a first period of time, and a second period of time, said periods of time being predetermined portions of a second immediately following the transmission of each pulse into said animal;

analyzing said echoes received during said first period of time by means of a first analyzer circuit within said housing to compare the characteristics of said echoes to a first set of characteristics corresponding to those caused by the tissue of said animal;

actuating a first indicator light on the outside of said housing in response to echo signals during said first time period having characteristics similar to said first set of characteristics;

analyzing said echoes received during said second period of time with a second analyzer circuit within said housing to compare the characteristics of said echo signals to a second set of characteristics corresponding to those characteristics caused by fluid surrounding a fetus within said animal;

actuating a second indicator light and a sound alarm mounted to said housing in response to echoes during said second time period having characteristics similar to said second set of characteristics.

* * * * *